(12) United States Patent
Jaeschke et al.

(10) Patent No.: US 9,199,971 B2
(45) Date of Patent: Dec. 1, 2015

(54) ARYLETHYNYL PYRIMIDINES

(71) Applicant: Hoffmann-La Roche Inc., Little Falls, NJ (US)

(72) Inventors: Georg Jaeschke, Basel (CH); Lothar Lindemann, Basel (CH); Heinz Stadler, Basel (CH); Eric Vieira, Frenkendorf (CH)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/622,232

(22) Filed: Feb. 13, 2015

(65) Prior Publication Data

US 2015/0158848 A1 Jun. 11, 2015

Related U.S. Application Data

(63) Continuation of application No. PCT/EP2013/066443, filed on Aug. 6, 2013.

(30) Foreign Application Priority Data

Aug. 13, 2012 (EP) .................................... 12180209

(51) Int. Cl.
C07D 403/04 (2006.01)
A61K 31/506 (2006.01)

(52) U.S. Cl.
CPC ............ *C07D 403/04* (2013.01); *A61K 31/506* (2013.01)

(58) Field of Classification Search
CPC ........................... C07D 403/04; A61K 31/506
USPC .......................................... 544/330; 514/275
See application file for complete search history.

(56) References Cited

FOREIGN PATENT DOCUMENTS

WO     WO 2011/128279     * 10/2011

OTHER PUBLICATIONS

Layzer, "Section Five-Degenerative Diseases of the Nervous System", Cecil Textbook of Medicine, 20th Edition, vol. 2 (1996), pp. 2050-2057.*
Damasio, "Alzheimer's Disease and Related Dementias", Cecil Textbook of Medicine, 20th Edition, vol. 2 (1996), pp. 1992-1996.*
Gross et al., Therapeutic Strategies in Fragile X Syndrome: Dysregulated mGluR Signaling and Beyond, Neuropsychopharmacology Reviews (2012) 37, pp. 178-195.*

* cited by examiner

*Primary Examiner* — Deepak Rao
(74) *Attorney, Agent, or Firm* — Tamara Kale

(57) ABSTRACT

The present invention relates to ethynyl derivatives of formula I

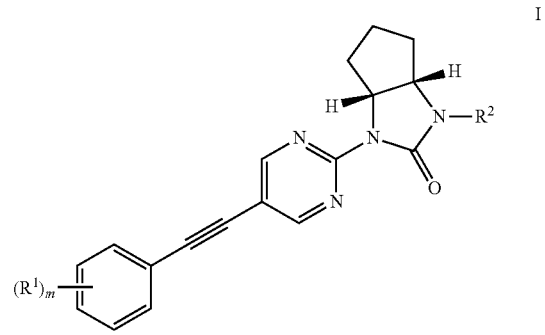

wherein
$R^1$ is hydrogen or halogen;
$R^2$ is $C_{1-3}$-alkyl or $-(CH_2)_n-O-CH_3$;
n is 2 or 3;
m is 1 or 2;
or to a pharmaceutically acceptable acid addition salt, to a racemic mixture, or to its corresponding enantiomer and/or optical isomer and/or stereoisomer thereof.
It has been found that the compounds of general formula I are allosteric modulators of the metabotropic glutamate receptor subtype 5 (mGluR5) with improved properties for the treatment of schizophrenia, cognitive diseases, fragile X syndrome or autism.

5 Claims, No Drawings

ARYLETHYNYL PYRIMIDINES

This application is a continuation of International Application No. PCT/EP2013/066443, filed on Aug. 6, 2013, which claims the benefit of EP 12180209.4, filed on Aug. 13, 2012, each of which is incorporated herein by reference in its entirety.

The present invention relates to ethynyl derivatives of formula I

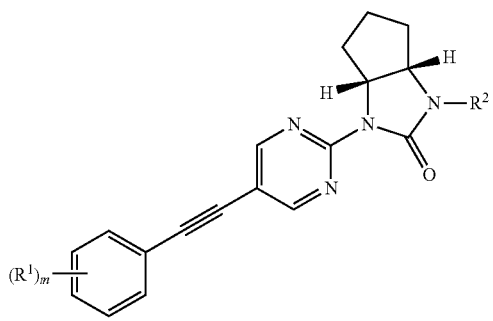

wherein
$R^1$ is hydrogen or halogen;
$R^2$ is $C_{1-3}$-alkyl or —$(CH_2)_n$—O—$CH_3$;
n is 2 or 3;
m is 1 or 2;
or to a pharmaceutically acceptable acid addition salt, to a racemic mixture, or to its corresponding enantiomer and/or optical isomer and/or stereoisomer thereof.

It has now surprisingly been found that the compounds of general formula I are allosteric modulators of the metabotropic glutamate receptor subtype 5 (mGluR5) which show advantageous biochemical-, physicochemical- and pharmacodynamic properties compared to compounds of prior art.

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), tuberous sclerosis (TSC), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

A new avenue for developing selective modulators is to identify compounds which act through allosteric mechanism, modulating the receptor by binding to a site different from the highly conserved orthosteric binding site. Allosteric modulators of mGluR5 have emerged recently as novel pharmaceutical entities offering this attractive alternative. Allosteric modulators have been described, for example in WO2008/151184, WO2006/048771, WO2006/129199, WO2005/044797 and in particular WO2011/128279 as well as in *Molecular Pharmacology*, 40, 333-336, 1991; *The Journal of Pharmacology and Experimental Therapeutics*, Vol 313, No. 1, 199-206, 2005;

Described in the prior art are positive allosteric modulators. They are compounds that do not directly activate receptors by themselves, but markedly potentiate agonist-stimulated responses, increase potency and maximum of efficacy. The binding of these compounds increases the affinity of a glutamate-site agonist at its extracellular N-terminal binding site. Allosteric modulation is thus an attractive mechanism for enhancing appropriate physiological receptor activation. There is a scarcity of selective allosteric modulators for the mGluR5 receptor. Conventional mGluR5 receptor modulators typically lack satisfactory aqueous solubility and exhibit poor oral bioavailability.

Therefore, there remains a need for compounds that overcome these deficiencies, and that effectively provide selective allosteric modulators for the mGluR5 receptor. The present invention solved this problem, as seen below:

Comparison of Compounds of the Invention Versus Similar Compounds of Prior Art:

Structurally similar compounds of prior art have been disclosed in WO2011128279 (=Ref. 1, Hoffmann-La Roche) and the structurally most similar compounds of this patent application (examples 106, 170 and 174) are shown for comparison. Example 106 of ref. 1 was disclosed as a racemic mixture. The chiral separation of this mixture was realized to yield the two enantiomers (using a separation procedure similar to that described in example 1, step 5). The most active (−) enantiomer as the comparative example has been selected. The same is true for example 170 of reference 1, and the optically pure (−) enantiomer will be used here for comparative purposes. For the sake of completion, example 174 is shown in its racemic form and corresponds exactly to example 174 of reference 1.

Comparison of Compounds of the Invention Vs. Reference Compound Ex. 106:

The compounds of the invention all show an over 200-fold higher solubility compared to the reference compound, despite the fact that the pyrimidine core is less basic than the pyridine core of example 106, and the $R^4$ groups are more lipophilic than the methyl group of the reference compound. This was an unexpected result and shows a clear advantage of the compounds of the present invention with respect to solubility, which is beneficial with respect to absorption, unbound free fraction and other drug-related pharmacological properties compared to structurally similar compounds of prior art.

Comparison of Compounds of the Invention Vs. Reference Compounds Ex. 170 and 174:

When compared to examples 170 and 174 of reference 1, the solubility values are also improved, although the reference compounds also have a diazine core. The main advantage however, is that the compounds of the invention do not show spontaneous addition to glutatione, indicative of Michael-addition type reactivity (GSH assay). The reaction of chemically reactive drugs with proteins (covalent protein binding—CVB) is an undesirable property with respect to drug safety. Proteins can form covalent adducts to drug molecules having Michael acceptor properties via their nucleophilic amino-acid side chains (e.g., cysteine, serine, lysine, etc.). Formation of drug-protein adducts can lead to undesired reactions of the immune system, which recognizes covalently bonded proteins as foreign. Such immune responses can lead to allergic reactions of varying intensity, called immune toxicity.

The "gold standard" CVB (covalent binding) assay, which detects the formation of covalent adducts by incubation of test compounds with liver microsomes needs to be conducted with $^{14}$C-labelled material. This is not appropriate for routine screening purposes. The spontaneous glutathione assay is appropriate for routine screening, and compounds that show significant Michael acceptor activity in the spontaneous glutathione assay are very likely to show activity in the CVB assay. Since the reactive species in this case is the parent drug and not a metabolically induced reactive metabolite, this is even of much greater importance. The above data show that compounds of the invention have a much lower tendency to form spontaneous covalent drug-glutathion adducts (NO FLAG) while the corresponding reference compounds form significant amounts of covalent drug-glutathion adducts due to their Michael acceptor properties (FLAG). Generally speaking, compounds of the present invention therefore have a clear advantage with respect to drug safety due to their much less pronounced Michael acceptor properties compared to structurally similar compounds of prior art.

LIST OF EXAMPLES

| Ex. | Structure | EC$_{50}$ (nM) mGlu5 PAM | Solubility [mg/ml] | GSH assay |
|---|---|---|---|---|
| Ref. 1 Ex. 106 | 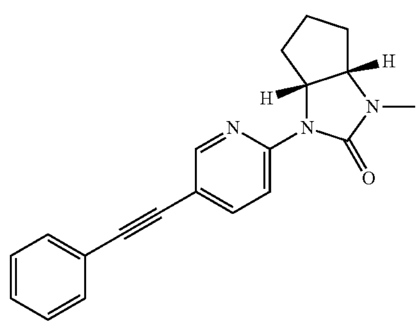 [SMILES: CN1C(=O)N(c2ccc(C#Cc3ccccc3)cn2)[C@@H]2CCC[C@@H]21] | 8.0 | 0.011 | |
| Ref. 1 Ex. 170 | 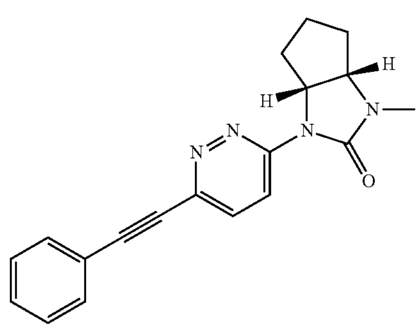 [SMILES: CN1C(=O)N(c2ccc(C#Cc3ccccc3)nn2)[C@@H]2CCC[C@@H]21] | 8.1 | 2 | FLAG |
| Ref. 1 Ex. 174 | [RACEMATE] | 11.9 | <1 | FLAG |

-continued

| Ex. | Structure | EC$_{50}$ (nM) mGlu5 PAM | Solubility [mg/ml] | GSH assay |
|---|---|---|---|---|
| 1 | (phenylethynyl-pyrimidinyl bicyclic imidazolidinone, N-ethyl) | 9.1 | 8 | NO FLAG |
| 2 | (3-fluorophenylethynyl-pyrimidinyl bicyclic imidazolidinone, N-ethyl) | 10.6 | 7 | NO FLAG |
| 3 | (4-fluorophenylethynyl-pyrimidinyl bicyclic imidazolidinone, N-ethyl) | 11.5 | 4 | NO FLAG |
| 4 | (2,5-difluorophenylethynyl-pyrimidinyl bicyclic imidazolidinone, N-ethyl) | 10 | 16 | NO FLAG |

-continued

| Ex. | Structure | EC$_{50}$ (nM) mGlu5 PAM | Solubility [mg/ml] | GSH assay |
|---|---|---|---|---|
| 5 | 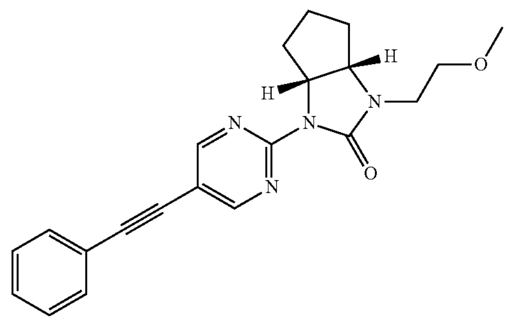 [SMILES: COCCN1C(=O)N(c2ncc(C#Cc3ccccc3)cn2)[C@@H]2CCC[C@@H]21] | 12.5 | 171 | NO FLAG |
| 6 | 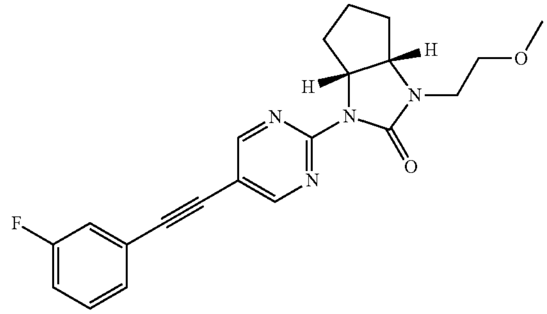 [SMILES: COCCN1C(=O)N(c2ncc(C#Cc3cccc(F)c3)cn2)[C@@H]2CCC[C@@H]21] | 24.5 | 114 | NO FLAG |
| 7 | 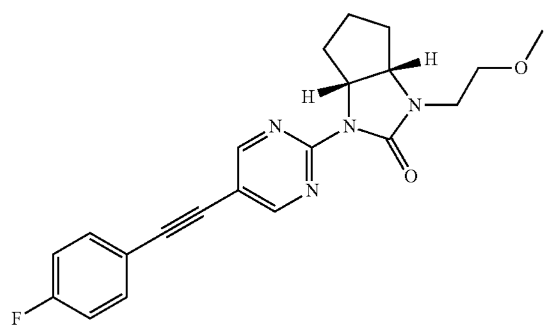 [SMILES: COCCN1C(=O)N(c2ncc(C#Cc3ccc(F)cc3)cn2)[C@@H]2CCC[C@@H]21] | 26.8 | 43 | NO FLAG |
| 8 | 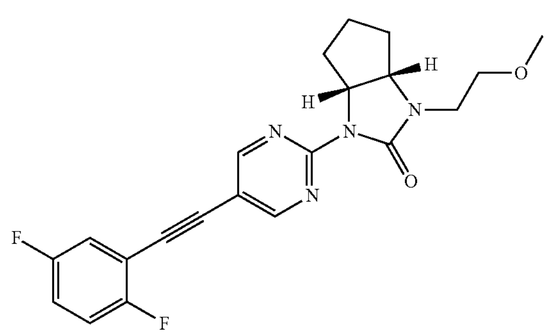 [SMILES: COCCN1C(=O)N(c2ncc(C#Cc3cc(F)ccc3F)cn2)[C@@H]2CCC[C@@H]21] | 15.7 | 75 | NO FLAG |

-continued

| Ex. | Structure | EC$_{50}$ (nM) mGlu5 PAM | Solubility [mg/ml] | GSH assay |
|---|---|---|---|---|
| 9 | 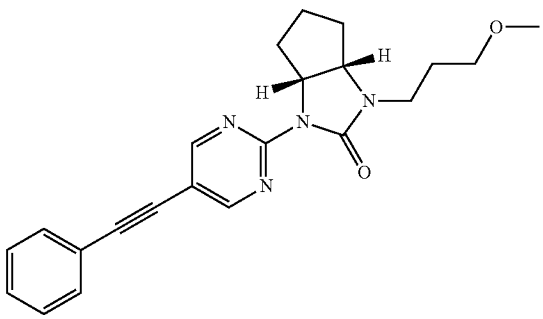 [SMILES: COCCCN1C(=O)N(c2ncc(C#Cc3ccccc3)cn2)[C@@H]2CCC[C@@H]21] | 30.9 | 153 | NO FLAG |
| 10 | 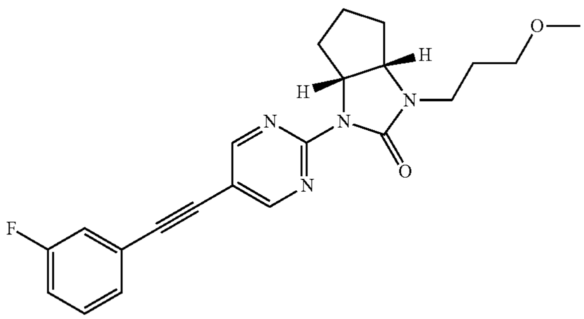 [SMILES: COCCCN1C(=O)N(c2ncc(C#Cc3cccc(F)c3)cn2)[C@@H]2CCC[C@@H]21] | 31.6 | 115 | NO FLAG |
| 11 | 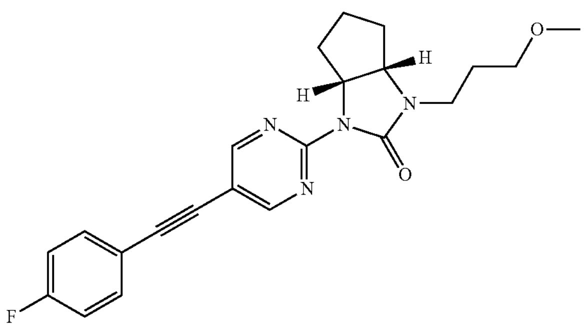 [SMILES: COCCCN1C(=O)N(c2ncc(C#Cc3ccc(F)cc3)cn2)[C@@H]2CCC[C@@H]21] | 35.0 | 56 | NO FLAG |

Lyophilisation Solubility Assay (LYSA)

The procedure of this automatic high throughput assay can be separated into two steps. First, DMSO stock solutions of test compounds are diluted in order to prepare four point calibration curves. The peak area at an optimal wavelength for each test compound is determined automatically by Ultra Fast Liquid Chromatography. The extraction of peak areas and retention times from the raw data is performed automatically. Using four concentrations and the related peak areas, slope and intercept of the calibration line is calculated. The correlation coefficient of the obtained regression line should be greater than 0.99. In the second phase, the sample solutions are prepared in duplicate from the DMSO stock solutions. The DMSO was removed using an evaporator. After evaporation of the DMSO, the solid drugs were solved in 0.05 M phosphate buffer (pH 6.5), stirred for one hour and afterwards shaken for two hours. After standing overnight (about 20 hours), the solutions are filtered using a microtiter filter plate. The filtrate and its 1/10 dilutions are then analyzed automatically by High Performance Liquid Chromatography (HPLC). The peak areas and retention times of the samples were extracted at the same wavelength used for the calibration.

The solubility is calculated using the following equation:

$$S = (A-b)/a \, (\times 10 \text{ for the sample diluted } 1/10)$$

Where S is the solubility in µg/mL; A is the peak area of the sample; a is the slope and b is the intercept of the calibration curve. Since this method is not optimal for values well below 1 µg/ml, the value (<1) is given for compounds where no substance peak is detected at the maximal dilution, which means the actual solubility is well below 1 µg/mL.

In the case of reference compound 106, the compound was equilibrated for 24 h in 0.05 M phosphate buffer (pH 6.5) using a procedure identical to that performed with the LYSA assay. The amount of solute present was then directly determined using manual conventional HPLC analytics.

Spontaneous Glutathione (GSH) Addition Assay

10 µM of test substance dissolved in pH 7.4 phosphate buffer was incubated with 5 mM GSH (glutathione) for 24 hours at room temperature. The samples were then analyzed using a mass spectrometer to determine whether adducts between glutathione and the drug had been formed. Samples for which the mass of a covalent adduct was clearly detected (M+307) are indicated as FLAG (positive). Compounds for which no adduct was detected are designated NO FLAG (negative).

Compounds of formula I are distinguished by having valuable therapeutic properties. They can be used in the treatment or prevention of disorders, relating to allosteric modulators for the mGluR5 receptor.

The most preferred indications for compounds which are allosteric modulators are schizophrenia and cognition.

The present invention relates to compounds of formula I and to their pharmaceutically acceptable salts, to these compounds as pharmaceutically active substances, to the processes for their production as well as to the use in the treatment or prevention of disorders, relating to allosteric modulators for the mGluR5 receptor, such as schizophrenia and cognition and to pharmaceutical compositions containing the compounds of formula I.

The following definitions of the general terms used in the present description apply irrespective of whether the terms in question appear alone or in combination.

The term "halogen" denotes chlorine, bromine, iodine or fluorine.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention is compounds of formula I

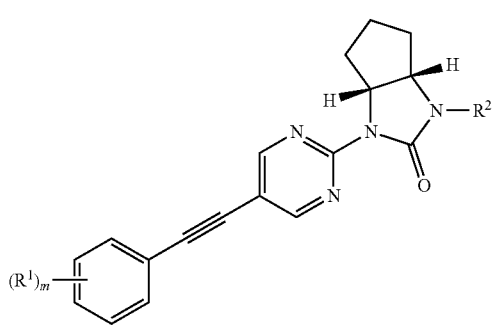

wherein
R$^1$ is hydrogen or fluoro;
R$^2$ is ethyl, —(CH$_2$)$_2$—OCH$_3$ or —(CH$_2$)$_3$—OCH$_3$;
m is 1 or 2;
or a pharmaceutically acceptable acid addition salt, a racemic mixture, or its corresponding enantiomer and/or optical isomer and/or stereoisomer thereof.

Examples of compounds of formula I are the followings:
(−)-(3aR,6aS)-1-Ethyl-3-(5-phenylethynyl-pyrimidin-2-yl)-hexahydro-cyclopentaimidazol-2-one
(−)-(3aR,6aS)-1-Ethyl-3-(5-(3-fluoro-phenylethynyl-pyrimidin-2-yl)-hexahydro-cyclopentaimidazol-2-one
(−)-(3aR,6aS)-1-Ethyl-3-(5-(4-fluoro-phenylethynyl-pyrimidin-2-yl)-hexahydro-cyclopentaimidazol-2-one
(−)-(3aR,6aS)-1-Ethyl-3-(5-(2,5-difluoro-phenylethynyl-pyrimidin-2-yl)-hexahydro-cyclopentaimidazol-2-one
(−)-(3aR,6aS)-1-(2-Methoxy-ethyl)-3-(5-phenylethynyl-pyrimidin-2-yl)-hexahydro-cyclopentaimidazol-2-one
(−)-(3aR,6aS)-1-(2-Methoxy-ethyl)-3-(5-(3-fluoro-phenylethynyl-pyrimidin-2-yl)-hexahydro-cyclopentaimidazol-2-one
(−)-(3aR,6aS)-1-(2-Methoxy-ethyl)-3-(5-(4-fluoro-phenylethynyl-pyrimidin-2-yl)-hexahydro-cyclopentaimidazol-2-one
(−)-(3aR,6aS)-1-(2-Methoxy-ethyl)-3-(5-(2,5-difluoro-phenylethynyl-pyrimidin-2-yl)-hexahydro-cyclopentaimidazol-2-one
(−)-(3aR,6aS)-1-(3-Methoxy-propyl)-3-(5-phenylethynyl-pyrimidin-2-yl)-hexahydro-cyclopentaimidazol-2-one
(−)-(3aR,6aS)-1-(3-Methoxy-propyl)-3-(5-(3-fluoro-phenylethynyl-pyrimidin-2-yl)-hexahydro-cyclopentaimidazol-2-one or
(−)-(3aR,6aS)-1-(3-Methoxy-propyl)-3-(5-(4-fluoro-phenylethynyl-pyrimidin-2-yl)-hexahydro-cyclopentaimidazol-2-one.

The preparation of compounds of formula I of the present invention may be carried out in sequential or convergent synthetic routes. Syntheses of the compounds of the invention are shown in the following schemes 1 and 2. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts may be prepared by methods, known in the art, for example by the process variant described below, which process comprises reacting a compound of formula II

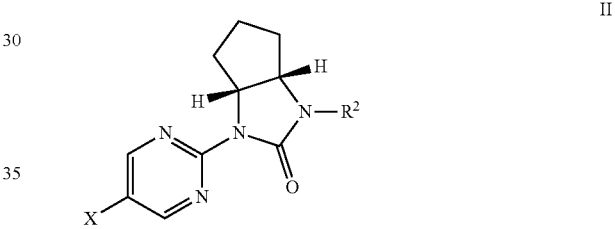

wherein X is a halogen atom selected from bromine or iodine with a suitable aryl-acetylene of formula III

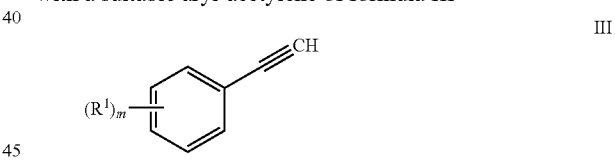

to form a compound of formula I

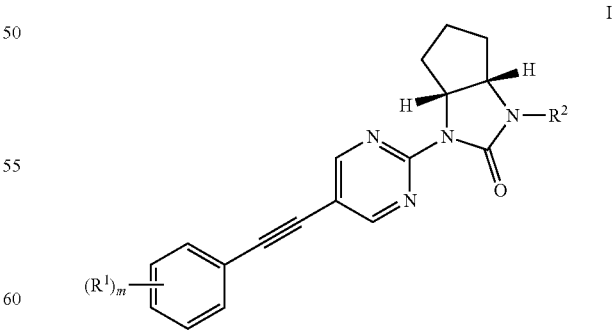

wherein the substituents are described above, or
if desired, converting the compounds obtained into pharmaceutically acceptable acid addition salts.

The preparation of compounds of formula I is further described in more detail in schemes 1 and 2 and in examples 1-11.

Scheme 1

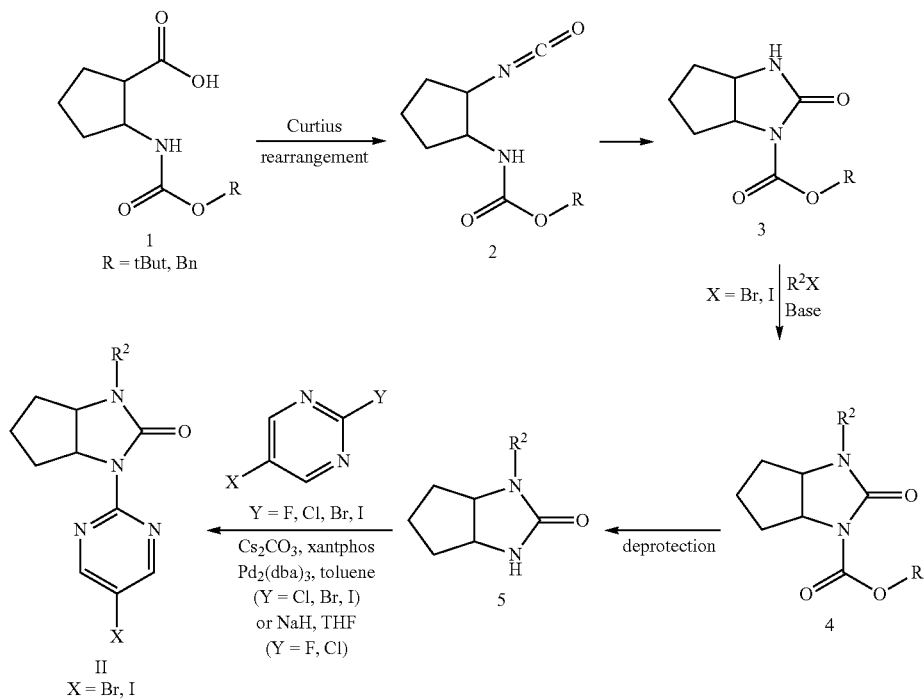

A halo-pyrimidine compound of formula II can be obtained by a Palladium catalyzed reaction of an appropriate dihalogenated pyrimidine such as 2-bromo-5-iodo-pyrimidine and an appropriate bicyclic urea of formula 5 (scheme 1). Reaction of a 2-Chloro- or 2-Fluoro-pyrimidine having a bromine or iodine in position 5 with a bicyclic urea of formula 5 can also form a compound of formula II by an aromatic nuclophilic substitution reaction using basic conditions such as for example NaH/THF or Cesium carbonate/DMF. The compound of formula 5 can be obtained starting from an appropriately protected cis-2-amino-cycloalkyl-1-carboxylic acid of formula 1 which is transformed via an acylazide intermediate into the corresponding isocyanate 2 (Curtius rearrangement) which then cyclizes to form the bicyclic urea compound 3. The free NH group of 3 can be alkylated according to standard procedures to form compound 4 which is then deprotected to yield the bicyclic urea 5. It is also possible to obtain optically pure intermediates starting from an optically pure protected acid of formula 1 or by separation of the racemic mixture at any stage of the synthesis using 'procedures known to persons skilled in the art.

Scheme 2

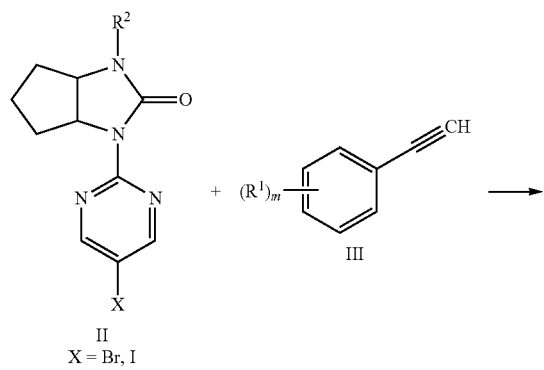

-continued

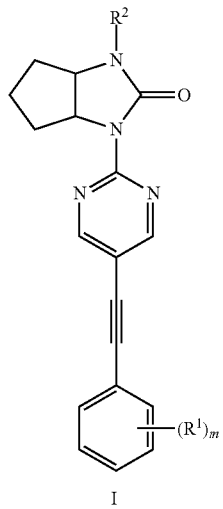

The compound of formula II (X=Br, I) may react with a suitable aryl-acetylene of formula III to form a compound of formula I, wherein the substituents are as described above and m is 1 or 2.

The compound of formula I as described herein as well as its pharmaceutically acceptable salt is used in the treatment or prevention of psychosis, epilepsy, schizophrenia, Alzheimer's disease, cognitive disorders and memory deficits, chronic and acute pain, restricted brain function caused by bypass operations or transplants, poor blood supply to the brain, spinal cord injuries, head injuries, hypoxia caused by pregnancy, cardiac arrest and hypoglycaemia, ischemia, Huntington's chorea, amyotrophic lateral sclerosis (ALS), dementia caused by AIDS, eye injuries, retinopathy, idiopathic parkinsonism or parkinsonism caused by medicaments, muscle spasms, convulsions, migraine, urinary incontinence, gastrointestinal reflux disorder, liver damage or failure whether drug or disease induced, Fragile-X syndrome, tuberulous sclerosis, Down syndrome, autism, nicotine addiction, opiate addiction, anxiety, vomiting, dyskinesia, eating disorders, in particular bulimia or anorexia nervosa, and depressions, particularly for the treatment and prevention of acute and/or chronic neurological disorders, anxiety, the treatment of chronic and acute pain, urinary incontinence and obesity.

The preferred indications are schizophrenia and cognitive disorders.

Present invention further relates to the use of a compound of formula I as described herein, as well as its pharmaceutically acceptable salt, for the manufacture of a medicament, preferably for the treatment and prevention of the above-mentioned disorders.

BIOLOGICAL ASSAY AND DATA

Intracellular $Ca^{2+}$ Mobilization Assay

A monoclonal HEK-293 cell line stably transfected with a cDNA encoding for the human mGlu5a receptor was generated; for the work with mGlu5 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 µg/ml hygromycin and 15 µg/ml blasticidin (all cell culture reagents and antibiotics from Invitrogen, Basel, Switzerland).

About 24 hrs before an experiment, $5 \times 10^4$ cells/well were seeded in poly-D-lysine coated, black/clear-bottomed 96-well plates. The cells were loaded with 2.5 µM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist L-glutamate was added to the cells at a concentration corresponding to $EC_{20}$ (typically around 80 µM) with on-line recording of fluorescence; in order to account for day-to-day variations in the responsiveness of cells, the $EC_{20}$ of glutamate was determined immediately ahead of each experiment by recording of a full dose-response curve of glutamate.

Responses were measured as peak increase in fluorescence minus basal (i.e. fluorescence without addition of L-glutamate), normalized to the maximal stimulatory effect obtained with saturating concentrations of L-glutamate. Graphs were plotted with the % maximal stimulatory using XLfit, a curve fitting program that iteratively plots the data using Levenburg Marquardt algorithm. The single site competition analysis equation used was $y=A+((B-A)/(1+((x/C)D)))$, where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (concentration at which half maximal stimulation was achieved), the Hill coefficient as well as the maximal response in % of the maximal stimulatory effect obtained with saturating concentrations of L-glutamate were calculated.

Positive signals obtained during the pre-incubation with the PAM test compounds (i.e. before application of an $EC_{20}$ concentration of L-glutamate) were indicative of an agonistic activity, the absence of such signals were demonstrating the lack of agonistic activities. A depression of the signal observed after addition of the $EC_{20}$ concentration of L-glutamate was indicative of an inhibitory activity of the test compound.

In the list of examples below are shown the corresponding results for compounds which all have $EC_{50}<30$ nM.

| Example | $EC_{50}$ (nM) mGlu5 PAM |
|---------|--------------------------|
| 1       | 9.1                      |
| 2       | 10.6                     |
| 3       | 11.5                     |
| 4       | 10.0                     |
| 5       | 12.5                     |
| 6       | 24.5                     |
| 7       | 26.8                     |
| 8       | 15.7                     |
| 9       | 30.9                     |
| 10      | 31.6                     |
| 11      | 35.0                     |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention Tablets of the following composition are produced in a conventional manner:

|  | mg/Tablet |
| --- | --- |
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example 1

(−)-(3aR,6aS)-1-Ethyl-3-(5-phenylethynyl-pyrimidin-2-yl)-hexahydro-cyclopentaimidazol-2-one

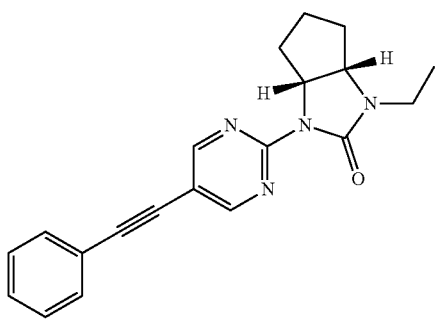 [SMILES: CCN1C(=O)N(c2ncc(C#Cc3ccccc3)cn2)[C@@H]2CCC[C@@H]21]

Step 1: (rac)-(3aSR,6aRS)-2-oxo-hexahydro-cyclopentaimidazole-1-carboxylic acid tert-butyl ester

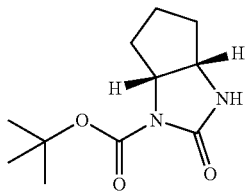 [SMILES: CC(C)(C)OC(=O)N1C(=O)N[C@H]2CCC[C@H]21]

A solution of (rac)-cis-2-(tert-butoxycarbonylamino)cyclopentanecarboxylic acid (CAS: 136315-70-3) (2.28 g, 9.98 mmol) and N-methylmorpholine (1.1 g, 1.21 ml, 11.0 mmol, 1.1 equiv.) in 28 ml of dichloroethane was stirred at r.t. for 10 min. Then diphenylphosphoric acid azide (3.02 g, 2.37 ml, 11.0 mmol, 1.1 equiv.) was added dropwise at room temperature and the colorless solution was stirred for 45 min at room temperature during which the solution turned light yellow. The solution was then warmed to 75° C. and stirred overnight and allowed to cool. After workup with dichloromethane/water, the combined organic phases were evaporated to dryness.

The orange solid was triturated with ethyl acetate and filtered to give 1.27 g of a white solid. The mother liquors were concentrated and the cristallized material was again filtered to yield an additional 0.55 g of product. One obtains a total yield of 1.82 g (81%) of the title compound as a crystalline white solid, MS: m/e=227.3 (M+H⁺).

Step 2: (rac)-(3aSR,6aRS)-3-Ethyl-2-oxo-hexahydro-cyclopentaimidazole-1-carboxylic acid tert-butyl ester

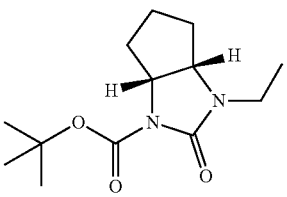 [SMILES: CCN1C(=O)N(C(=O)OC(C)(C)C)[C@@H]2CCC[C@@H]21]

To a solution of (3aSR,6aRS)-2-oxo-hexahydro-cyclopentaimidazole-1-carboxylic acid tert-butyl ester (Example 1, step 1) (1.50 g, 6.63 mmol) in 25 ml of DMF was added a 60% suspension of sodium hydride in mineral oil (207 mg, 8.62 mmol, 1.3 equiv.). The suspension was stirred for 45 minutes at room temperature (gas evolution), then iodoethane (1.34 g, 0.696 ml, 8.62 mmol, 1.3 equiv.) was added and the mixture was stirred at room temperature overnight. After concentration in vaccuo and workup with ethyl acetate/water, 1.60 g of a yellow oil were obtained containing mineral-oil drops which was directly used in the next step without further characterization.

Step 3: (rac)-(3aRS,6aSR)-1-Ethyl-hexahydro-cyclopentaimidazol-2-one

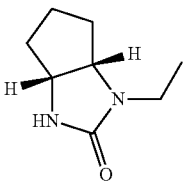

To a solution of (3aSR,6aRS)-3-methyl-2-oxo-hexahydro-cyclopentaimidazole-1-carboxylic acid tert-butyl ester (Example 1, step 2) (1.60 g, 6.29 mmol) in 15 ml of dichloromethane was added trifluoroacetic acid (5.74 g, 3.9 ml, 50.3 mmol, 8 equiv.) and the yellow solution was stirred for 15 h at room temperature. The reaction mixture was quenched by addition of saturated sodium bicarbonate solution and the pH of the aqueous phase was set to 9. After workup with dichloromethane/water, the organic phases were dried, filtered and concentrated in vaccuo to yield 0.801 g of a yellow oil, which directly used in the next step without further characterization.

Step 4: (rac)-(3aSR,6aRS)-1-(5-Bromo-pyrimidin-2-yl)-3-Ethyl-hexahydro-cyclopentaimidazol-2-one

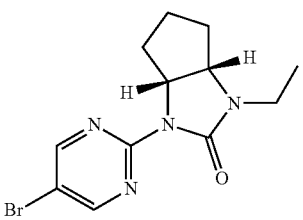 [SMILES: CCN1C(=O)N(c2ncc(Br)cn2)[C@@H]2CCC[C@@H]21]

To a suspension of 2-bromo-5-iodopyrimidine (340 mg, 1.19 mmol), (3aR,6aS)-1-methylhexahydrocyclopenta[d]imidazol-2(1H)-one (Example 1, step 3) (184 mg, 1.19 mmol, 1.0 equiv.), 622 mg cesium carbonate (1.9 mmol, 2 equiv.), and 4,5-bis(diphenylphosphino)-9,9-dimethylxanthene (xantphos) 28 mg, 0.048 mmol, 0.04 equiv.) in 8 ml of toluene was added under argon atmosphere tris(dibenzylideneacetone)dipalladium(0) (Pd$_2$(dba)$_3$) (22 mg, 0.024 mmol, 0.02 equiv.). The mixture was stirred overnight at 50° C. The mixture was directly loaded on a 20 g silicagel column and was eluted with a 20% to 80% ethylacetate in heptane gradient to yield the title compound (229 mg, 62%) as a light-brown solid, MS: m/e=311.1, 313.0 (M+H$^+$).

Step 5: (rac)-(3aRS,6aSR)-1-Ethyl-3-(5-phenylethynyl-pyrimidin-2-yl)-hexahydro-cyclopentaimidazol-2-one In a microwave tube were dissolved 80 mg (0.26 mmol) of (rac)-1-(5-bromopyrimidin-2-yl)-3-ethylhexahydrocyclopenta[d]imidazol-2(1H)-one (Example 1, step 4) in 3 ml DMF. Argon was bubbled through the solution. Ethynylbenzene (57 μl, 53 mg, 0.52 mmol, 2 equiv.), Bis(triphenylphosphine)palladium(II) chloride (9 mg, 0.013 mmol, 0.05 equiv.), copper (I) iodide (1.5 mg, 7.7 μmol, 0.03 equiv.), triphenylphosphine (2.0 mg, 7.7 μmol, 0.03 equiv.) and 107 μl of triethylamine (78 mg, 0.77 mmol, 3 equiv.) were added. The dark brown solution was stirred at 75° C. overnight, adsorbed on silica and purified by flash chromatography (silica gel, 20 g, 0% to 80% EtOAc in heptane gradient) to yield 72.7 mg (85%) of the title compound as a brown solid, MS: m/e=333.3 (M+H$^+$).

Step 6: (−)-(3aR,6aS)-1-Ethyl-3-(5-phenylethynyl-pyrimidin-2-yl)-hexahydro-cyclopentaimidazol-2-one The racemic mixture of (−)-(3aR,6aS)- and (+)-(3aS,6aR)-1-ethyl-3-(5-phenylethynyl-pyrimidin-2-yl)-hexahydro-cyclopentaimidazol-2-one (70 mg) was separated by chiral HPLC: (Reprosil Chiral NR—5 cm×50 cm, 20 μM; 40% Ethanol/heptane, 35 ml/min, 18 Bar). Peak detection was realized using a UV-detector as well as an optical rotation detector (ORD) where one peak has a negative signal (the (−)-enantiomer), and the other peak has a positive signal (the (+)-enantiomer). The (−)-enantiomer (30.5 mg) was obtained as an off-white solid, MS: m/e=333.3 (M+H$^+$).

The (+)-enantiomer (26.7 mg) was obtained as an off-white solid, MS: m/e=333.3 (M+H$^+$).

Example 2

(−)-(3aR,6aS)-1-Ethyl-3-(5-(3-fluoro-phenylethynyl-pyrimidin-2-yl)-hexahydro-cyclopentaimidazol-2-one

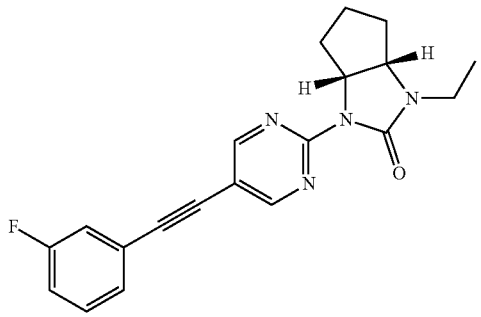 [SMILES: CCN1C(=O)N(c2ncc(C#Cc3cccc(F)c3)cn2)[C@@H]2CCC[C@@H]21]

The title compound was prepared in accordance with the general method of Example 1, step 5 starting from (rac)-1-(5-bromopyrimidin-2-yl)-3-ethylhexahydrocyclopenta[d]imidazol-2(1H)-one (Example 1, step 4) and 1-ethynyl-3-fluorobenzene to yield 72.4 mg (80%) of racemic material ((+/−)-(3aRS,6aSR)-1-ethyl-3-(5-(3-fluoro-phenylethynyl-pyrimidin-2-yl)-hexahydro-cyclopentaimidazol-2-one) as a light brown solid; MS: m/e=351.3 (M+H$^+$) which was then separated by chiral HPLC using similar separation conditions as described in example 1, step 6 to yield the enantiomerically pure enantiomer (−)-(3aR,6aS)-1-ethyl-3-(5-(3-fluoro-phenylethynyl-pyrimidin-2-yl)-hexahydro-cyclopentaimidazol-2-one as a light yellow semi-solid; MS: m/e=351.3 (M+H$^+$) and its enantiomer (+)-(3aS,6aR)-1-ethyl-3-(5-(3-fluoro-phenylethynyl-pyrimidin-2-yl)-hexahydro-cyclopentaimidazol-2-one as a light yellow solid; MS: m/e=351.3 (M+H$^+$).

Example 3

(−)-(3aR,6aS)-1-Ethyl-3-(5-(4-fluoro-phenylethynyl-pyrimidin-2-yl)-hexahydro-cyclopentaimidazol-2-one

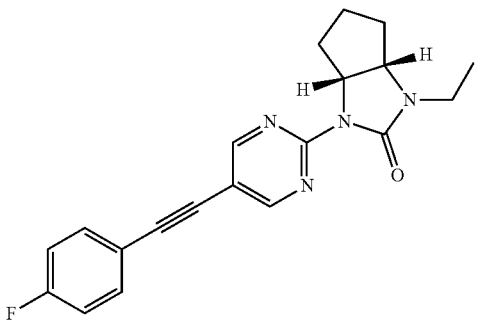 [SMILES: CCN1C(=O)N(c2ncc(C#Cc3ccc(F)cc3)cn2)[C@@H]2CCC[C@@H]21]

The title compound was prepared in accordance with the general method of Example 1, step 5 starting from (rac)-1-(5-bromopyrimidin-2-yl)-3-ethylhexahydrocyclopenta[d]imidazol-2(1H)-one (Example 1, step 4) and 1-ethynyl-4-fluorobenzene to yield racemic material ((+/−)-(3aRS,6aSR)-1-ethyl-3-(5-(4-fluoro-phenylethynyl-pyrimidin-2-yl)-hexahydro-cyclopentaimidazol-2-one) as an off-white solid; MS: m/e=351.3 (M+H$^+$). Separation using chiral HPLC and similar separation conditions as described in examples 1 and 2 yielded the enantiomerically pure enantiomers (−)-(3aR,6aS)-1-ethyl-3-(5-(4-fluoro-phenylethynyl-pyrimidin-2-yl)-hexahydro-cyclopentaimidazol-2-one as an off-white solid; MS: m/e=351.3 (M+H$^+$) and (+)-(3aS,6aR)-1-ethyl-3-(5-(4-fluoro-phenylethynyl-pyrimidin-2-yl)-hexahydro-cyclopentaimidazol-2-one as an off-white solid; MS: m/e=351.3 (M+H$^+$).

Example 4

(−)-(3aR,6aS)-1-Ethyl-3-(5-(2,5-difluoro-phenylethynyl-pyrimidin-2-yl)-hexahydro-cyclopentaimidazol-2-one

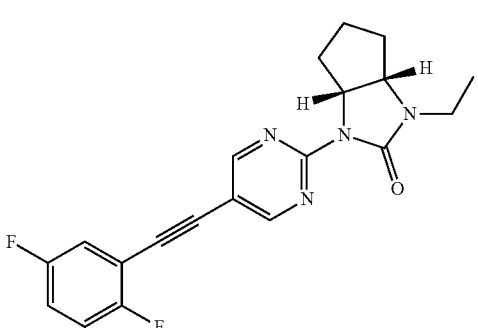

21

The title compound was prepared in accordance with the general method of Example 1, step 5 starting from (rac)-1-(5-bromopyrimidin-2-yl)-3-ethylhexahydrocyclopenta[d]imidazol-2(1H)-one (Example 1, step 4) and 1-ethynyl-2,5-difluorobenzene to yield racemic material ((+/−)-(3aRS,6aSR)-1-ethyl-3-(5-(2,5-difluoro-phenylethynyl-pyrimidin-2-yl)-hexahydro-cyclopentaimidazol-2-one) as a light brown solid; MS: m/e=369.2 (M+H$^+$). Separation using chiral HPLC and similar separation conditions as described in example 1 yielded the enantiomerically pure enantiomers (−)-(3aR,6aS)-1-ethyl-3-(5-(2,5-difluoro-phenylethynyl-pyrimidin-2-yl)-hexahydro-cyclopentaimidazol-2-one as a yellow oil; MS: m/e=369.2 (M+H$^+$) and (+)-(3aS,6aR)-1-ethyl-3-(5-(2,5-difluoro-phenylethynyl-pyrimidin-2-yl)-hexahydro-cyclopentaimidazol-2-one as a yellow oil; MS: m/e=369.2 (M+H$^+$).

Example 5

(−)-(3aR,6aS)-1-(2-Methoxy-ethyl)-3-(5-phenylethynyl-pyrimidin-2-yl)-hexahydro-cyclopentaimidazol-2-one

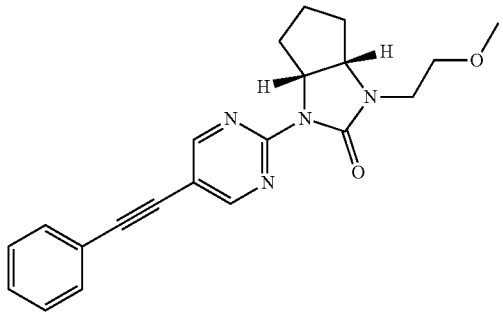 [SMILES: COCCN1C(=O)N(c2ncc(C#Cc3ccccc3)cn2)[C@@H]2CCC[C@@H]21]

Step 1: (rac)-(3aSR,6aRS)-3-(2-Methoxy-ethyl)-2-oxo-hexahydro-cyclopentaimidazole-1-carboxylic acid tert-butyl ester

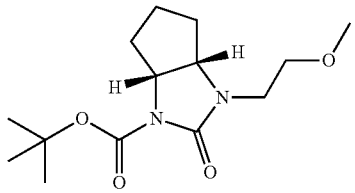 [SMILES: COCCN1C(=O)N(C(=O)OC(C)(C)C)[C@@H]2CCC[C@@H]21]

The title compound was prepared in accordance with the general method of example 1, step 2 starting from (rac)-(3aSR,6aRS)-2-oxo-hexahydro-cyclopentaimidazole-1-carboxylic acid tert-butyl ester (Example 1, step 1) and using 1-bromo-2-methoxyethane instead of iodoethane to yield the desired product as a light yellow oil which was directly used in the next step without further characterisation.

22

Step 2: (rac)-(3aRS,6aSR)-1-(2-Methoxy-ethyl)-hexahydro-cyclopentaimidazol-2-one

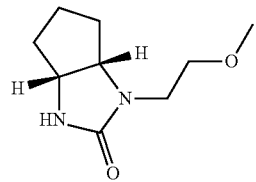

The title compound was prepared in accordance with the general method of example 1, step 3 starting from (rac)-(3aSR,6aRS)-3-(2-methoxy-ethyl)-2-oxo-hexahydro-cyclopentaimidazole-1-carboxylic acid tert-butyl ester (Example 10, step 1) to yield the desired product as a light yellow oil which was directly used in the next step without further characterisation.

Step 3: (rac)-(3aSR,6aRS)-1-(5-Bromo-pyrimidin-2-yl)-3-(2-methoxy-ethyl)-hexahydro-cyclopentaimidazol-2-one

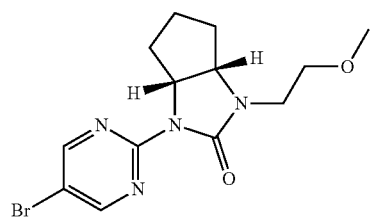 [SMILES: COCCN1C(=O)N(c2ncc(Br)cn2)[C@@H]2CCC[C@@H]21]

The title compound was prepared in accordance with the general method of example 1, step 4 by reaction of (rac)-(3aSR,6aRS)-3-(2-methoxy-ethyl)-2-oxo-hexahydro-cyclopentaimidazole-1-carboxylic acid tert-butyl ester (Example 10, step 2) and 2-bromo-5-iodopyrimidine to yield the desired product as a light-brown solid, MS: m/e=341.0, 343.1 (M+H$^+$).

Step 4: (rac)-(3aRS,6aSR)-1-(2-Methoxy-ethyl)-3-(5-phenylethynyl-pyrimidin-2-yl)-hexahydro-cyclopentaimidazol-2-one The title compound was prepared in accordance with the general method of Example 1, step 5 starting from (rac)-(3aSR,6aRS)-1-(5-bromo-pyrimidin-2-yl)-3-(2-methoxy-ethyl)-hexahydro-cyclopentaimidazol-2-one (Example 10, step 3) and ethynylbenzene to yield racemic (rac)-(3aRS,6aSR)-1-(2-methoxy-ethyl)-3-(5-phenylethynyl-pyrimidin-2-yl)-hexahydro-cyclopentaimidazol-2-one as an light yellow oil; MS: m/e=363.3 (M+H$^+$).

Step 5: (−)-(3aR,6aS)-1-(2-Methoxy-ethyl)-3-(5-phenylethynyl-pyrimidin-2-yl)-hexahydro-cyclopentaimidazol-2-one Separation using chiral HPLC and similar separation conditions as described in example 1 yielded the enantiomerically pure enantiomers (−)-(3aR,6aS)-1-(2-methoxy-ethyl)-3-(5-phenylethynyl-pyrimidin-2-yl)-hexahydro-cyclopentaimidazol-2-one as an amorphous yellow solid; MS: m/e=363.3 (M+H$^+$) and (+)-(3aS,6aR)-1-(2-methoxy-ethyl)-3-(5-phenylethynyl-pyrimidin-2-yl)-hexahydro-cyclopentaimidazol-2-one as an amorphous yellow solid; MS: m/e=363.3 (M+H$^+$).

Example 6

(−)-(3aR,6aS)-1-(2-Methoxy-ethyl)-3-(5-(3-fluoro-phenylethynyl-pyrimidin-2-yl)-hexahydro-cyclopentaimidazol-2-one

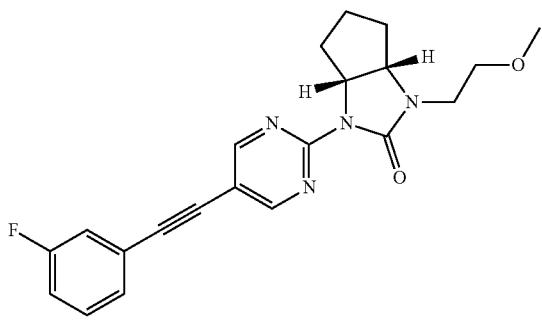 [SMILES: COCCN1C(=O)N(c2ncc(C#Cc3cccc(F)c3)cn2)[C@@H]2CCC[C@@H]21]

The title compound was prepared in accordance with the general method of Example 1, step 5 starting from (rac)-(3aSR,6aRS)-1-(5-bromo-pyrimidin-2-yl)-3-(2-methoxy-ethyl)-hexahydro-cyclopentaimidazol-2-one (Example 5, step 3) and 1-ethynyl-3-fluorobenzene to yield racemic material ((+/−)-(3aRS,6aSR)-1-(2-methoxy-ethyl)-3-(5-(3-fluoro-phenylethynyl-pyrimidin-2-yl)-hexahydro-cyclopentaimidazol-2-one as a light brown oil; MS: m/e=381.3 (M+H$^+$) which was then separated by chiral HPLC using similar separation conditions as described in example 1 to yield the enantiomerically pure enantiomers (−)-(3aR,6aS)-1-(2-methoxy-ethyl)-3-(5-(3-fluoro-phenylethynyl-pyrimidin-2-yl)-hexahydro-cyclopentaimidazol-2-one as an amorphous yellow solid; MS: m/e=381.3 (M+H+) and (+)-(3aS, 6aR1-(2-methoxy-ethyl)-3-(5-(3-fluoro-phenylethynyl-pyrimidin-2-yl)-hexahydro-cyclopentaimidazol-2-one as an amorphous yellow solid; MS: m/e=381.3 (M+H$^+$).

Example 7

(−)-(3aR,6aS)-1-(2-Methoxy-ethyl)-3-(5-(4-fluoro-phenylethynyl-pyrimidin-2-yl)-hexahydro-cyclopentaimidazol-2-one

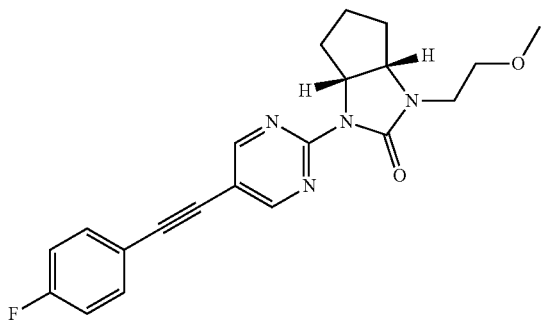 [SMILES: COCCN1C(=O)N(c2ncc(C#Cc3ccc(F)cc3)cn2)[C@@H]2CCC[C@@H]21]

The title compound was prepared in accordance with the general method of Example 1, step 5 starting from (rac)-1-(5-bromopyrimidin-2-yl)-3-(2-methoxy-ethyl)-hexahydro-cyclopenta[d]imidazol-2(1H)-one (Example 5, step 3) and 1-ethynyl-4-fluorobenzene to yield racemic material ((+/−)-(3aRS,6aSR)-1-(2-methoxy-ethyl)-3-(5-(4-fluoro-phenyl-ethynyl-pyrimidin-2-yl)-hexahydro-cyclopentaimidazol-2-one as an off-white solid; MS: m/e=381.3 (M+H$^+$). Separation using chiral HPLC and similar separation conditions as described in example 1 yielded the enantiomerically pure enantiomers (−)-(3aR,6aS)-1-(2-methoxy-ethyl)-3-(5-(4-fluoro-phenylethynyl-pyrimidin-2-yl)-hexahydro-cyclopentaimidazol-2-one as an off-white solid; MS: m/e=381.3 (M+H$^+$) and (+)-(3aS,6aR)-1-(2-methoxy-ethyl)-3-(5-(4-fluoro-phenylethynyl-pyrimidin-2-yl)-hexahydro-cyclopentaimidazol-2-one as an off-white solid; MS: m/e=381.3 (M+H$^+$).

Example 8

(−)-(3aR,6aS)-1-(2-Methoxy-ethyl)-3-(5-(2,5-difluoro-phenylethynyl-pyrimidin-2-yl)-hexahydro-cyclopentaimidazol-2-one

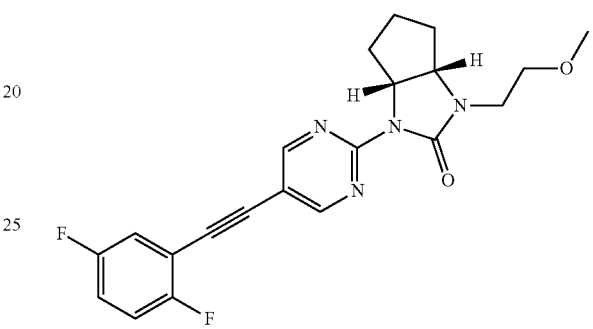

The title compound was prepared in accordance with the general method of Example 1, step 5 starting from (rac)-1-(5-bromopyrimidin-2-yl)-3-(2-methoxy-ethyl)-hexahydro-cyclopenta[d]imidazol-2(1H)-one (Example 5, step 3) and 1-ethynyl-2,5-difluorobenzene to yield racemic material ((+/−)-(3aRS,6aSR)-1-(2-methoxy-ethyl)-3-(5-(2,5-difluoro-phenyl-ethynyl-pyrimidin-2-yl)-hexahydro-cyclopentaimidazol-2-one as a light brown solid; MS: m/e=399.2 (M+H$^+$). Separation using chiral HPLC and similar separation conditions as described in example 1 yielded the enantiomerically pure enantiomers (−)-(3aR,6aS)-1-(2-methoxy-ethyl)-3-(5-(2,5-difluoro-phenylethynyl-pyrimidin-2-yl)-hexahydro-cyclopentaimidazol-2-one as an off-white solid; MS: m/e=399.2 (M+H$^+$) and (+)-(3aS,6aR)-1-(2-methoxy-ethyl)-3-(5-(2,5-difluoro-phenylethynyl-pyrimidin-2-yl)-hexahydro-cyclopentaimidazol-2-one as a light yellow oil which solidified on standing; MS: m/e=399.2 (M+H$^+$).

Example 9

(−)-(3aR,6aS)-1-(3-Methoxy-propyl)-3-(5-phenylethynyl-pyrimidin-2-yl)-hexahydro-cyclopentaimidazol-2-one

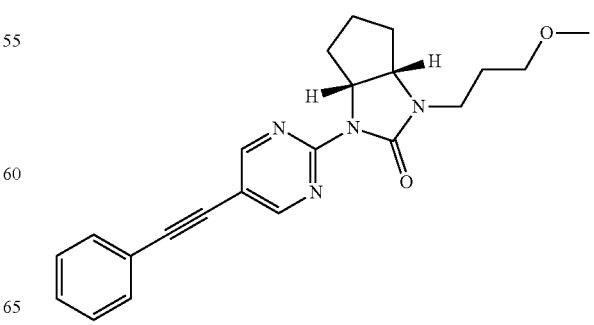

Step 1: (rac)-(3aSR,6aRS)-3-(3-Methoxy-propyl)-2-oxo-hexahydro-cyclopentaimidazole-1-carboxylic acid tert-butyl ester

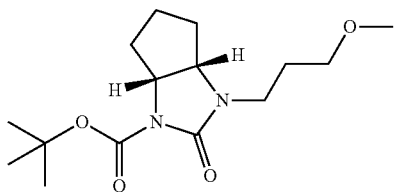 [SMILES: COCCCN1C(=O)N(C(=O)OC(C)(C)C)[C@@H]2CCC[C@@H]21]

The title compound was prepared in accordance with the general method of example 1, step 2 starting from (rac)-(3aSR,6aRS)-2-oxo-hexahydro-cyclopentaimidazole-1-carboxylic acid tert-butyl ester (Example 1, step 1) and using 1-bromo-3-methoxypropane instead of iodoethane to yield the desired product as a light yellow oil which was directly used in the next step without further characterisation.

Step 2: (rac)-(3aRS,6aSR)-1-(3-Methoxy-propyl)-hexahydro-cyclopentaimidazol-2-one

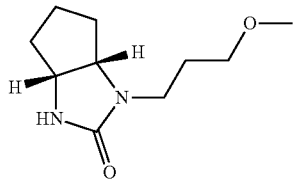

The title compound was prepared in accordance with the general method of example 1, step 3 starting from (rac)-(3aSR,6aRS)-3-(3-methoxy-propyl)-2-oxo-hexahydro-cyclopentaimidazole-1-carboxylic acid tert-butyl ester (Example 9, step 2) to yield the desired product as a light brown oil which was directly used in the next step without further characterisation.

Step 3: (rac)-(3aRS,6aSR)-1-(3-Methoxy-propyl)-3-(5-phenylethynyl-pyrimidin-2-yl)-hexahydro-cyclopentaimidazol-2-one In a 10 mL pyrex tube, 2-bromo-5-(phenylethynyl)pyrimidine (CAS: 1338493-52-9)(80 mg, 309 µmol, Eq: 1.00) and (rac)-(3aRS,6aSR)-1-(3-Methoxy-propyl)-hexahydro-cyclopentaimidazol-2-one (68.0 mg, 309 µmol, 1.0 equiv.) were dissolved in 2 ml of Toluene. Cesium carbonate (201 mg, 618 µmol, 2.0 equiv.), Xanthphos (7.15 mg, 12.4 µmol, 0.04 equiv.) and $Pd_2(dba)_3$ (5.65 mg, 6.18 µmol, 0.02 equiv.) were added and the red-brown reaction mixture was stirred at 90° C. for 3 hr. The reaction mixture was filtered, adsorbed on silica, and purified by flash chromatography (silica gel, 20 g with 1 g Silica-NH2, 30% to 100% EtOAc in heptane gradient at 301 nm). One obtained 65.6 mg of the title compound as a yellow oil; MS: m/e=377.6 (M+H$^+$).

Step 5: (−)-(3aR,6aS)-1-(3-Methoxy-propyl)-3-(5-phenylethynyl-pyrimidin-2-yl)-hexahydro-cyclopentaimidazol-2-one Separation using chiral HPLC and similar separation conditions as described in example 1 yielded the enantiomerically pure enantiomers (−)-(3aR,6aS)-1-(3-methoxy-propyl)-3-(5-phenylethynyl-pyrimidin-2-yl)-hexahydro-cyclopentaimidazol-2-one as an amorphous yellow solid; MS: m/e=377.6 (M+H$^+$) and (+)-(3aS,6aR)-1-(3-methoxy-propyl)-3-(5-phenylethynyl-pyrimidin-2-yl)-hexahydro-cyclopentaimidazol-2-one as an amorphous yellow solid; MS: m/e=377.6 (M+H$^+$).

Example 10

(−)-(3aR,6aS)-1-(3-Methoxy-propyl)-3-(5-(3-fluoro-phenylethynyl-pyrimidin-2-yl)-hexahydro-cyclopentaimidazol-2-one

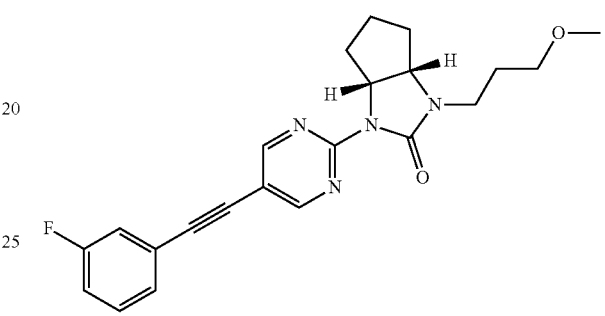

Step 1: (rac)-(3aSR,6aRS)-1-(5-Bromo-pyrimidin-2-yl)-3-(3-methoxy-propyl)-hexahydro-cyclopentaimidazol-2-one

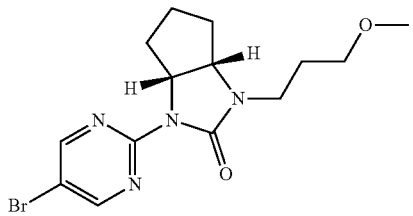 [SMILES: COCCCN1C(=O)N(c2ncc(Br)cn2)[C@@H]2CCC[C@@H]21]

The title compound was prepared in accordance with the general method of example 1, step 4 by reaction of (rac)-(3aSR,6aRS)-3-(3-methoxy-propyl)-2-oxo-hexahydro-cyclopentaimidazole-1-carboxylic acid tert-butyl ester (Example 9, step 2) and 2-Bromo-5-iodopyrimidine, which after workup and purification by flash chromatography (silica gel, 35% to 90% EtOAc in heptane gradient) yielded the desired product as a yellow oil, which was directly used in the next step without further charaterisation.

Step 2: (−)-(3aR,6aS)-1-(3-Methoxy-propyl)-3-(5-(3-fluoro-phenylethynyl-pyrimidin-2-yl)-hexahydro-cyclopentaimidazol-2-one The title compound was prepared in accordance with the general method of Example 1, step 5 starting from (rac)-(3aSR,6aRS)-1-(5-Bromo-pyrimidin-2-yl)-3-(3-methoxy-propyl)-hexahydro-cyclopentaimidazol-2-one and 1-Ethynyl-3-fluorobenzene to yield racemic material ((+/−)-(3aRS,6aSR)-1-(3-methoxy-propyl)-3-(5-(3-fluoro-phenylethynyl-pyrimidin-2-yl)-hexahydro-cyclopentaimidazol-2-one as a brown oil; MS: m/e=395.6 (M+H$^+$) which was then separated

Example 11

(−)-(3aR,6aS)-1-(3-Methoxy-propyl)-3-(5-(4-fluoro-phenylethynyl-pyrimidin-2-yl)-hexahydro-cyclopentaimidazol-2-one

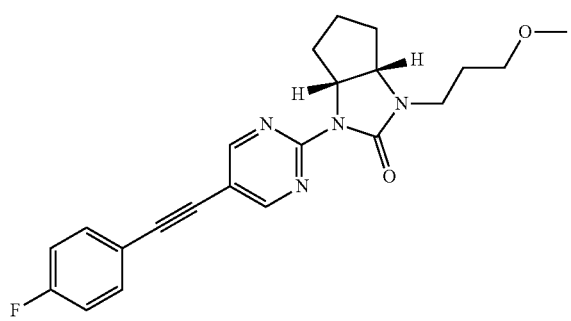 [SMILES: COCCCN1C(=O)N(c2ncc(C#Cc3ccc(F)cc3)cn2)[C@@H]2CCC[C@@H]21]

The title compound was prepared in accordance with the general method of Example 1, step 5 starting from (rac)-(3aSR,6aRS)-1-(5-Bromo-pyrimidin-2-yl)-3-(3-methoxy-propyl)-hexahydro-cyclopentaimidazol-2-one and 1-Ethynyl-4-fluorobenzene to yield racemic material ((+/−)-(3aRS, 6aSR)-1-(3-methoxy-propyl)-3-(5-(3-fluoro-phenylethynyl-pyrimidin-2-yl)-hexahydro-cyclopentaimidazol-2-one as a brown oil; MS: m/e=395.6 (M+H+) which was then separated by chiral HPLC using similar separation conditions as described in example 1 to yield the enantiomerically pure enantiomers (−)-(3aR,6aS)-1-(3-methoxy-propyl)-3-(5-(3-fluoro-phenylethynyl-pyrimidin-2-yl)-hexahydro-cyclopentaimidazol-2-one as an orange oil; MS: m/e=395.6 (M+H+) and (+)-(3aS,6aR1-(3-methoxy-propyl)-3-(5-(3-fluoro-phenylethynyl-pyrimidin-2-yl)-hexahydro-cyclopentaimidazol-2-one as an orange oil; MS: m/e=395.6 (M+H$^+$).

The invention claimed is:

1. An ethynyl derivative of formula I

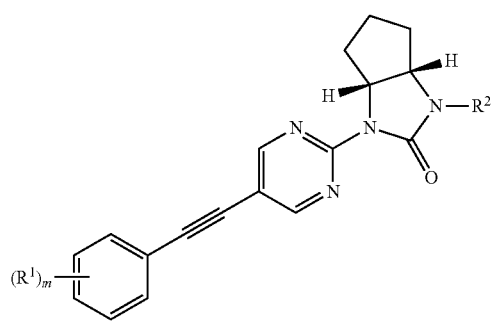

wherein
R$^1$ is hydrogen or halogen;
R$^2$ is C$_{1-3}$-alkyl or —(CH$_2$)$_n$—O—CH$_3$;
n is 2 or 3;
m is 1 or 2;
or a pharmaceutically acceptable acid addition salt and/or optical isomer and/or stereoisomer thereof.

2. An ethynyl derivative of formula I according to claim 1

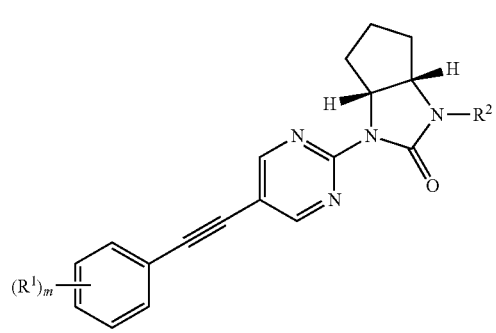

wherein
R$^1$ is hydrogen or fluoro;
R$^2$ is ethyl, —(CH$_2$)$_2$—OCH$_3$ or —(CH$_2$)$_3$—OCH$_3$;
m is 1 or 2;
or a pharmaceutically acceptable acid addition salt and/or optical isomer and/or stereoisomer thereof.

3. An ethynyl derivative of formula I according to claim 1, wherein the compound is selected from the group consisting of:

(−)-(3aR,6aS)-1-Ethyl-3-(5-phenylethynyl-pyrimidin-2-yl)-hexahydro-cyclopentaimidazol-2-one (−)-(3aR,6aS)-1-Ethyl-3-(5-(3-fluoro-phenylethynyl-pyrimidin-2-yl)-hexahydro-cyclopentaimidazol-2-one (−)-(3aR,6aS)-1-Ethyl-3-(5-(4-fluoro-phenylethynyl-pyrimidin-2-yl)-hexahydro-cyclopentaimidazol-2-one (−)-(3aR,6aS)-1-Ethyl-3-(5-(2,5-difluoro-phenylethynyl-pyrimidin-2-yl)-hexahydro-cyclopentaimidazol-2-one (−)-(3aR,6aS)-1-(2-Methoxy-ethyl)-3-(5-phenylethynyl-pyrimidin-2-yl)-hexahydro-cyclopentaimidazol-2-one (−)-(3aR,6aS)-1-(2-Methoxy-ethyl)-3-(5-(3-fluoro-phenylethynyl-pyrimidin-2-yl)-hexahydro-cyclopentaimidazol-2-one (−)-(3aR,6aS)-1-(2-Methoxy-ethyl)-3-(5-(4-fluoro-phenylethynyl-pyrimidin-2-yl)-hexahydro-cyclopentaimidazol-2-one (−)-(3aR,6aS)-1-(2-Methoxy-ethyl)-3-(5-(2,5-difluoro-phenylethynyl-pyrimidin-2-yl)-hexahydro-cyclopentaimidazol-2-one (−)-(3aR,6aS)-1-(3-Methoxy-propyl)-3-(5-phenylethynyl-pyrimidin-2-yl)-hexahydro-cyclopentaimidazol-2-one (−)-(3aR,6aS)-1-(3-Methoxy-propyl)-3-(5-(3-fluoro-phenylethynyl-pyrimidin-2-yl)-hexahydro-cyclopentaimidazol-2-one and (−)-(3aR,6aS)-1-(3-Methoxy-propyl)-3-(5-(4-fluoro-phenylethynyl-pyrimidin-2-yl)-hexahydro-cyclopentaimidazol-2-one.

4. A process for preparation of a compound of formula I as described in claim 1, comprising reacting a compound of formula II

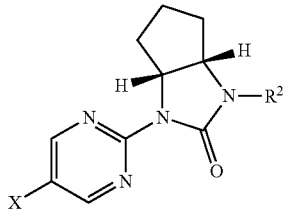

II wherein X is a halogen atom selected from bromine or iodine with a suitable aryl-acetylene of formula III

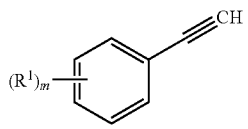

III to form a compound of formula I

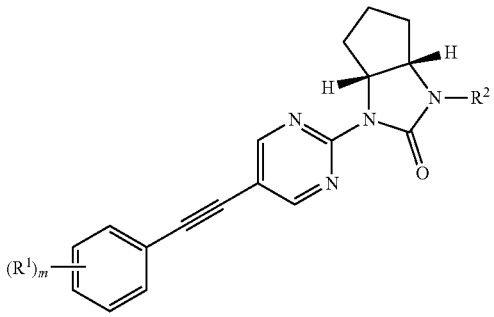

I wherein the substituents are described above, or if desired, converting the compounds obtained into pharmaceutically acceptable acid addition salts.

5. A pharmaceutical composition comprising a compound of formula I of claim 1 as well as its pharmaceutically acceptable salt.

* * * * *